United States Patent
Lietz et al.

(10) Patent No.: US 9,023,052 B2
(45) Date of Patent: May 5, 2015

(54) ULNA OSTEOTOMY SYSTEM

(75) Inventors: Eva Lietz, Solothurn (CH); Dirk Kerstan, Solothurn (CH); Ladislav Nagy, Kilchberg (CH)

(73) Assignee: Depuy Synthes Products, Inc., Raynham, MA (US)

( * ) Notice: Subject to any disclaimer, the term of this patent is extended or adjusted under 35 U.S.C. 154(b) by 170 days.

(21) Appl. No.: 13/014,414

(22) Filed: Jan. 26, 2011

(65) Prior Publication Data

US 2012/0123484 A1 May 17, 2012

Related U.S. Application Data

(60) Provisional application No. 61/310,406, filed on Mar. 4, 2010.

(51) Int. Cl.
*A61B 17/58* (2006.01)
*A61B 17/80* (2006.01)
*A61B 17/14* (2006.01)
*A61B 17/15* (2006.01)
*A61B 17/17* (2006.01)

(52) U.S. Cl.
CPC .............. *A61B 17/8057* (2013.01); *A61B 17/14* (2013.01); *A61B 17/141* (2013.01); *A61B 17/151* (2013.01); *A61B 17/1728* (2013.01); *A61B 17/8014* (2013.01); *A61B 17/809* (2013.01); *A61B 17/148* (2013.01); *A61B 17/1739* (2013.01)

(58) Field of Classification Search
USPC ......... 606/70–71, 280–299, 79, 82, 86 R, 87, 606/96
See application file for complete search history.

(56) References Cited

U.S. PATENT DOCUMENTS

| 4,929,247 | A | | 5/1990 | Rayhack |
| 5,176,685 | A | | 1/1993 | Rayhack |
| 5,709,686 | A | | 1/1998 | Talos et al. |
| 5,722,978 | A | * | 3/1998 | Jenkins, Jr. ..................... 606/87 |
| 6,001,099 | A | * | 12/1999 | Huebner ....................... 606/281 |
| 6,007,535 | A | | 12/1999 | Rayhack et al. |
| 6,066,142 | A | * | 5/2000 | Serbousek et al. .............. 606/96 |

(Continued)

FOREIGN PATENT DOCUMENTS

| CN | 2724645 | 9/2005 |
| CN | 101466317 | 6/2009 |

(Continued)

*Primary Examiner* — Christian Sevilla
*Assistant Examiner* — Eric S Gibson
(74) *Attorney, Agent, or Firm* — Fay Kaplun & Marcin, LLP

(57) ABSTRACT

A bone plate includes a first three-part combination hole extending through a proximal portion of the plate, a first portion configured to engage a threaded head portion of a bone fixation element, a second portion configured to receive a bone fixation element along an axis substantially perpendicular to a longitudinal axis of the bone and a third portion defining a screw axis extending toward the distal end of the elongated body at a non-perpendicular angle relative to the longitudinal axis in combination with a first two-part combination hole extending through the proximal portion, a first threaded portion configured to engage a threaded head portion of a bone fixation element and a second portion defining an elongated slot extending along a longitudinal axis of the plate for receiving a bone fixation element so that the plate may slide along its longitudinal axis relative to the bone fixation element.

18 Claims, 14 Drawing Sheets

(56) References Cited

U.S. PATENT DOCUMENTS

| | | |
|---|---|---|
| 6,689,139 B2 | 2/2004 | Horn |
| 7,540,874 B2 * | 6/2009 | Trumble et al. ............... 606/79 |
| 2004/0181228 A1 * | 9/2004 | Wagner et al. ................ 606/69 |
| 2005/0245935 A1 * | 11/2005 | Casey et al. .................. 606/82 |
| 2006/0095044 A1 | 5/2006 | Grady, Jr. et al. |
| 2006/0264946 A1 * | 11/2006 | Young ........................... 606/69 |
| 2007/0055249 A1 * | 3/2007 | Jensen et al. ................. 606/69 |
| 2007/0270850 A1 * | 11/2007 | Geissler ........................ 606/69 |
| 2007/0276383 A1 * | 11/2007 | Rayhack ....................... 606/69 |
| 2008/0140130 A1 * | 6/2008 | Chan et al. .................. 606/280 |
| 2009/0254126 A1 * | 10/2009 | Orbay et al. ................ 606/282 |
| 2010/0168799 A1 | 7/2010 | Schumer |

FOREIGN PATENT DOCUMENTS

| | | |
|---|---|---|
| EP | 1990017 | 11/2008 |
| FR | 2 846 870 | 5/2004 |
| GB | 2 334 214 | 8/1999 |
| JP | 2007/500069 | 1/2007 |
| WO | 96/29948 | 10/1996 |
| WO | 2004/084701 | 10/2004 |
| WO | 2006/091827 | 8/2006 |
| WO | 2007/127994 | 11/2007 |
| WO | 2008/007196 | 1/2008 |
| WO | 2008/089336 | 7/2008 |

* cited by examiner

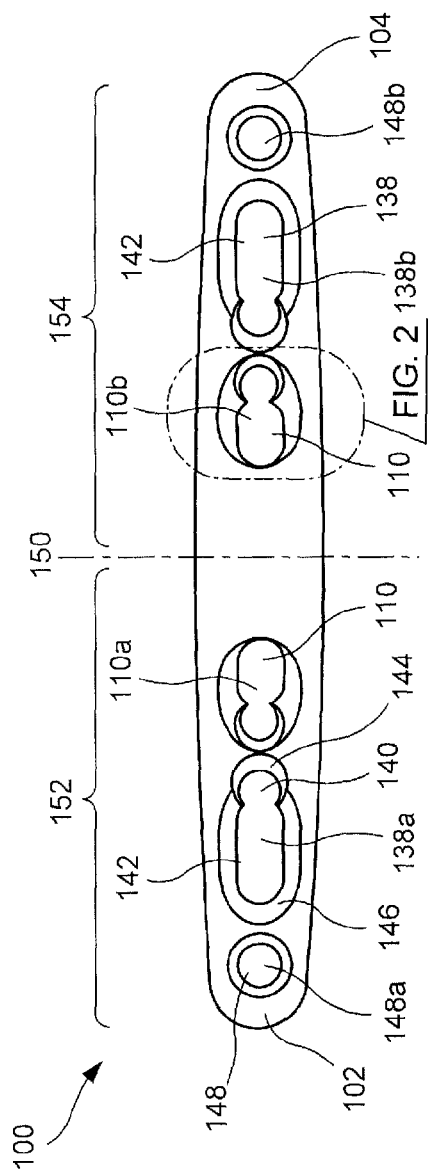
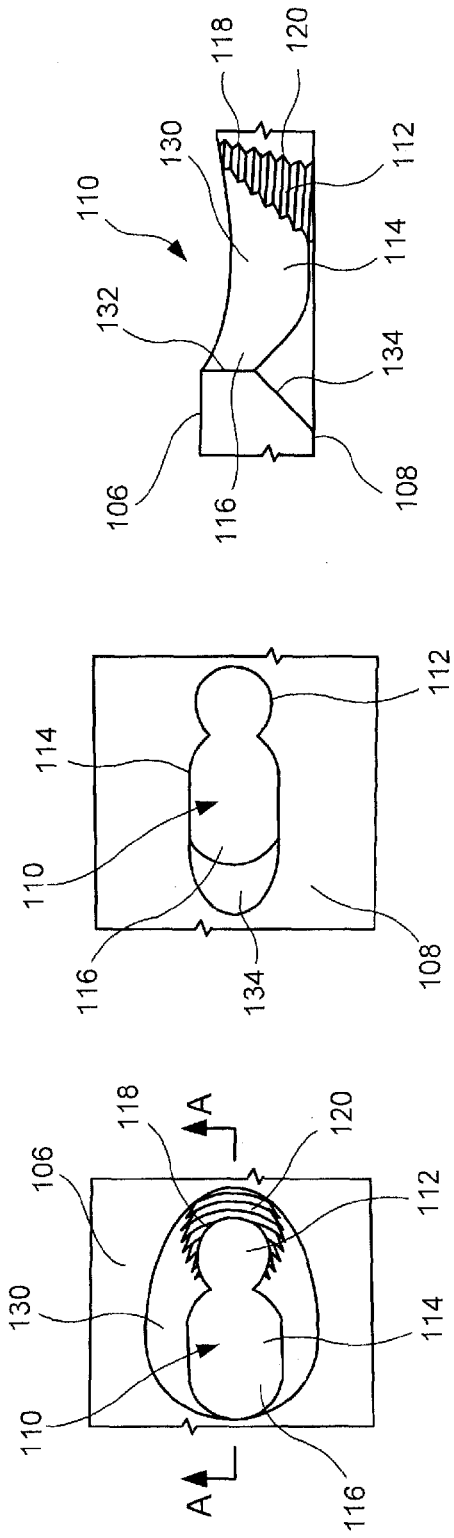

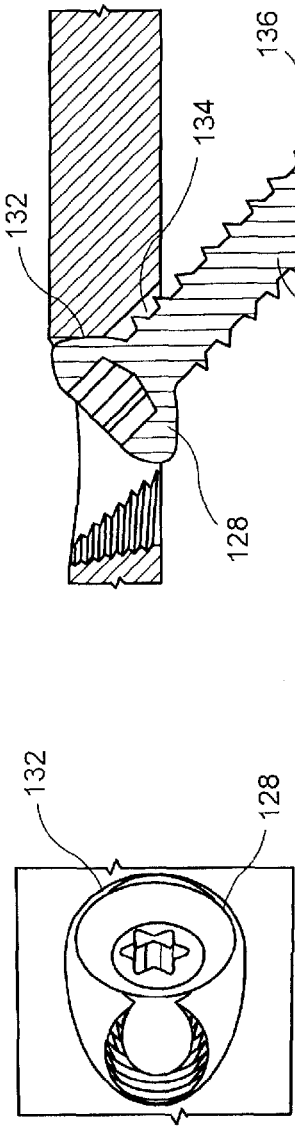
FIG. 7A
FIG. 7B
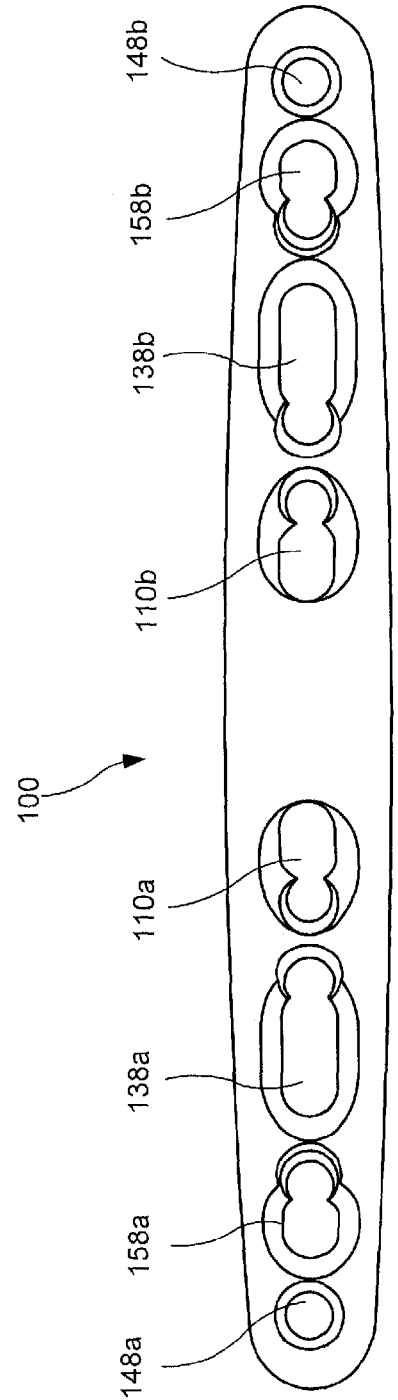
FIG. 8

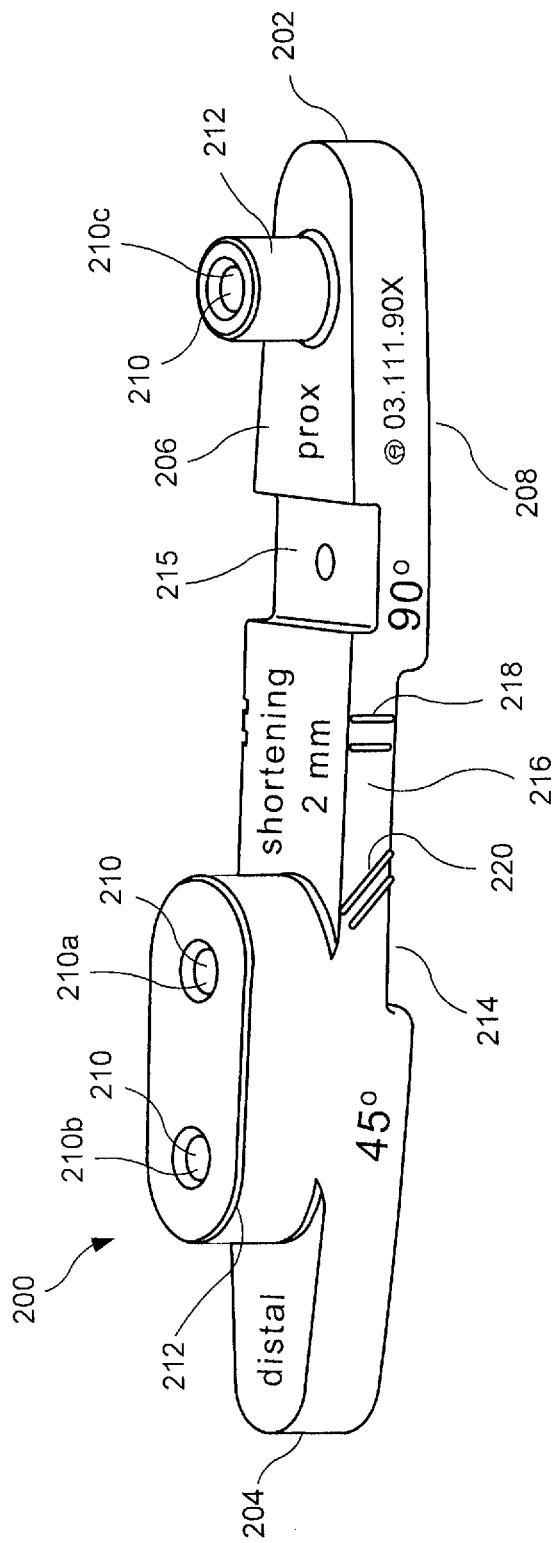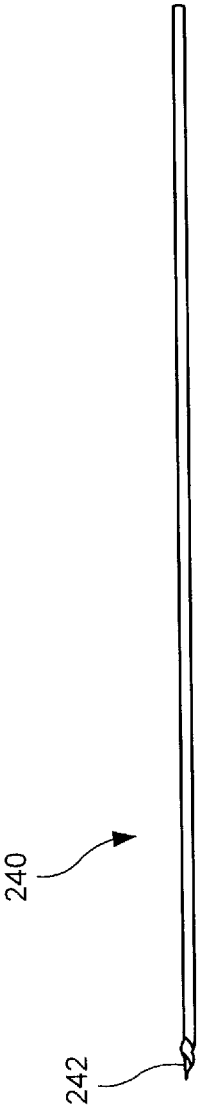
FIG. 11
FIG. 12

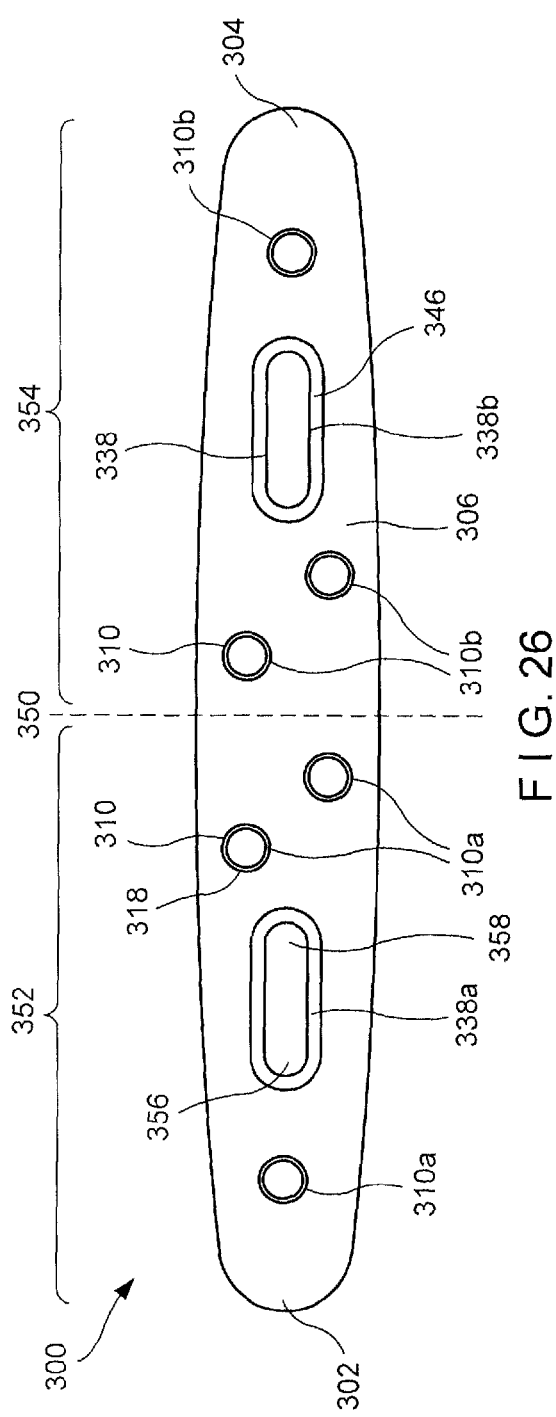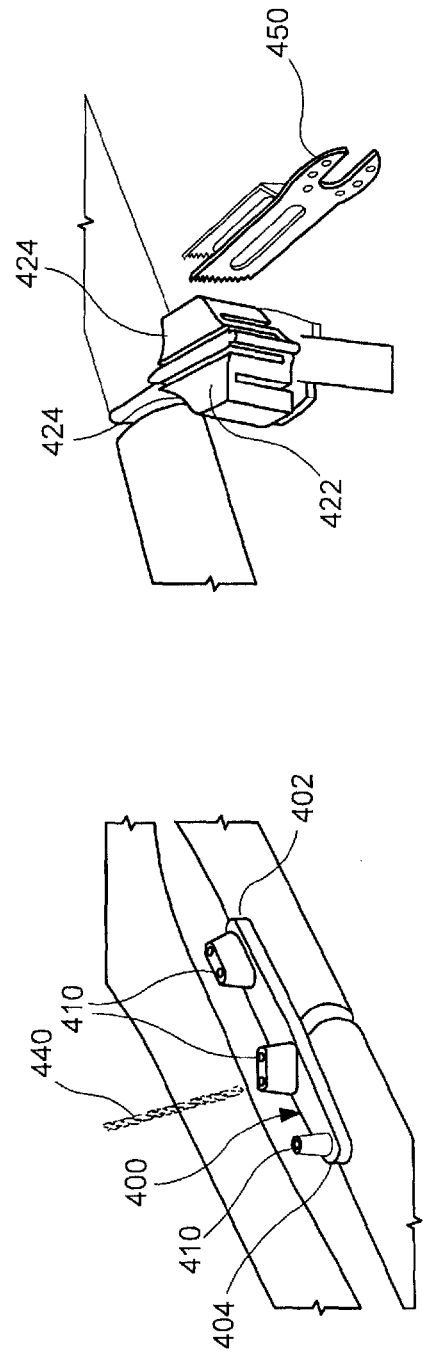
FIG. 26
FIG. 28
FIG. 27

US 9,023,052 B2

ULNA OSTEOTOMY SYSTEM

PRIORITY CLAIM

The present application claims priority to U.S. Provisional Application Ser. No. 61/310,406 filed on Mar. 4, 2010 and entitled "Ulna Osteotomy System," the entire disclosure of which is incorporated herein by reference.

FIELD OF THE INVENTION

The present invention relates to systems and methods for performing an osteotomy and, in particular, an osteotomy plate and other devices such as a drill guide for providing accurate alignment of cut portions of a bone.

BACKGROUND

An osteotomy is a surgical procedure in which a bone is cut to shorten, lengthen and/or change an alignment of the bone. In particular, an ulna shortening osteotomy cuts the ulna to treat symptoms such as wrist pain, swelling, limited range of motion and diminished grip strength, which may result from conditions such as ulnar impaction syndrome. Ulnar impaction syndrome is a degenerative condition related to excessive load bearing across the ulnar aspect of the wrist and chronic impingement of the ulnar head against the TFCC, lunate and triquetrum. By shortening the ulna, impaction is reduced preventing wrist pain, swelling, etc., such that function of the wrist joint is regained. Current ulna osteotomy systems require complex surgical techniques with complex instrumentation resulting in delayed unions or non-unions caused by inaccurate osteotomies and/or difficulty in maintaining bone alignment. In addition, the osteotomy systems often contain bulky instruments and implants, resulting in hardware irritation and often, implant removal.

SUMMARY OF THE INVENTION

The present invention is directed to a bone plate, comprising an elongated body extending from a proximal end to a distal end and including a first surface which, when in an operative position, faces away from a bone on which the plate is to be mounted and a second surface which, when in the operative position, faces the bone and a first three-part combination hole extending through a proximal portion of the plate, a first portion of the first three-part combination hole being threaded and configured to engage a threaded head portion of a bone fixation element, a second portion thereof configured to receive a bone fixation element along an axis substantially perpendicular to a longitudinal axis of the bone when the plate is mounted thereon in a desired orientation and a third portion defining a screw axis extending from the second surface toward the distal end of the elongated body at a non-perpendicular angle relative to the longitudinal axis of the bone when the plate is mounted thereon in a desired orientation in combination with a first two-part combination hole extending through the proximal portion of the plate, a first threaded portion thereof being configured to receive and engage a threaded head portion of a bone fixation element and a second portion thereof defining an elongated slot extending along a longitudinal axis of the plate for receiving a bone fixation element therethrough so that the plate may slide along its longitudinal axis relative to the bone fixation element received therethrough.

BRIEF DESCRIPTION OF THE DRAWINGS

FIG. 1 shows a top plan view of an osteotomy plate according to an exemplary embodiment of the present invention;

FIG. 2 shows an enlarged top view of a three-part hole of the plate of FIG. 1;

FIG. 3 shows an enlarged bottom view of the three-part hole of FIG. 2;

FIG. 4 shows an enlarged cross-sectional view of the three-part hole of FIG. 2, taken along line A-A;

FIG. 7A shows an enlarged top view of the three-part hole of FIG. 2 including a bone fixation element inserted therethrough, in a third configuration;

FIG. 7B shows an enlarged cross-sectional view of the three-part hole and bone fixation element of FIG. 7A;

FIG. 8 shows a top plan view of a further embodiment of the plate of FIG. 1;

FIG. 11 shows a perspective view of a drill template according to an exemplary embodiment of the present invention;

FIG. 12 shows a side view of a guide wire according to an exemplary embodiment of the present invention;

FIG. 26 shows a top plan view of a bone plate according to another exemplary embodiment of the present invention;

FIG. 27 shows a perspective view of a drill template mounted to a bone according to the exemplary embodiment of FIG. 26;

FIG. 28 shows a perspective view of a saw guide according to the exemplary embodiment of FIG. 26;

DETAILED DESCRIPTION

Figure 5A:
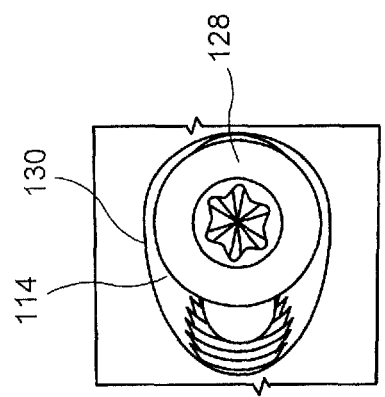
FIG. 5A shows an enlarged top view of the three-part hole of FIG. 2 including a bone fixation element inserted therethrough, in a first configuration.

The present invention may be further understood with reference to the following description and the appended drawings, wherein like elements are referred to with the same reference numerals. The present invention relates to systems and methods for performing an osteotomy. In particular, exemplary embodiments describe an osteotomy plate and other devices such as a drill guide for providing accurate alignment of cut portions of a bone. It will be understood by those of skill in the art that, although exemplary embodiments specifically describe an ulnar osteotomy, the present invention may be used for osteotomies of other bones as well.

Figure 13:
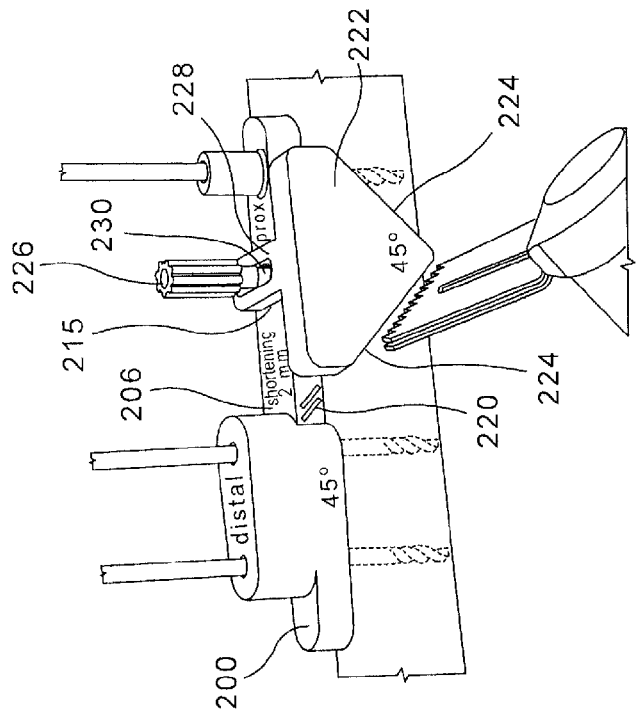
FIG. 13 shows a perspective view of a saw guide according to an exemplary embodiment of the present invention.
Figure 14:
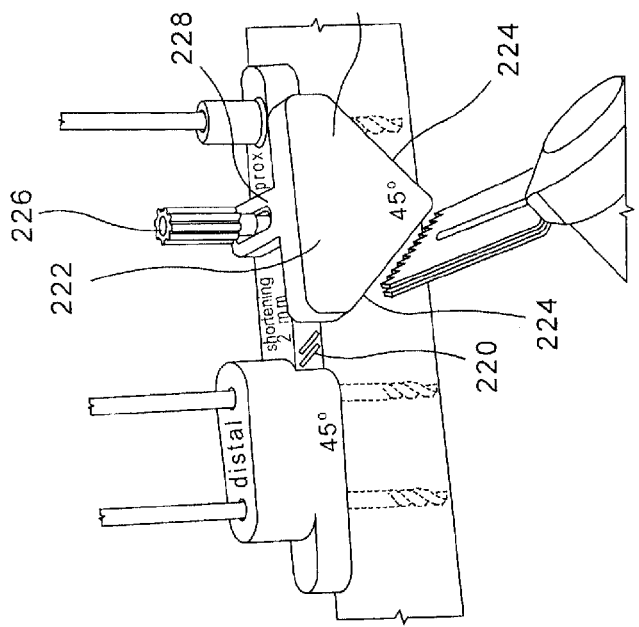
FIG. 14 shows a perspective view of the saw guide of FIG. 13.
Figure 16:
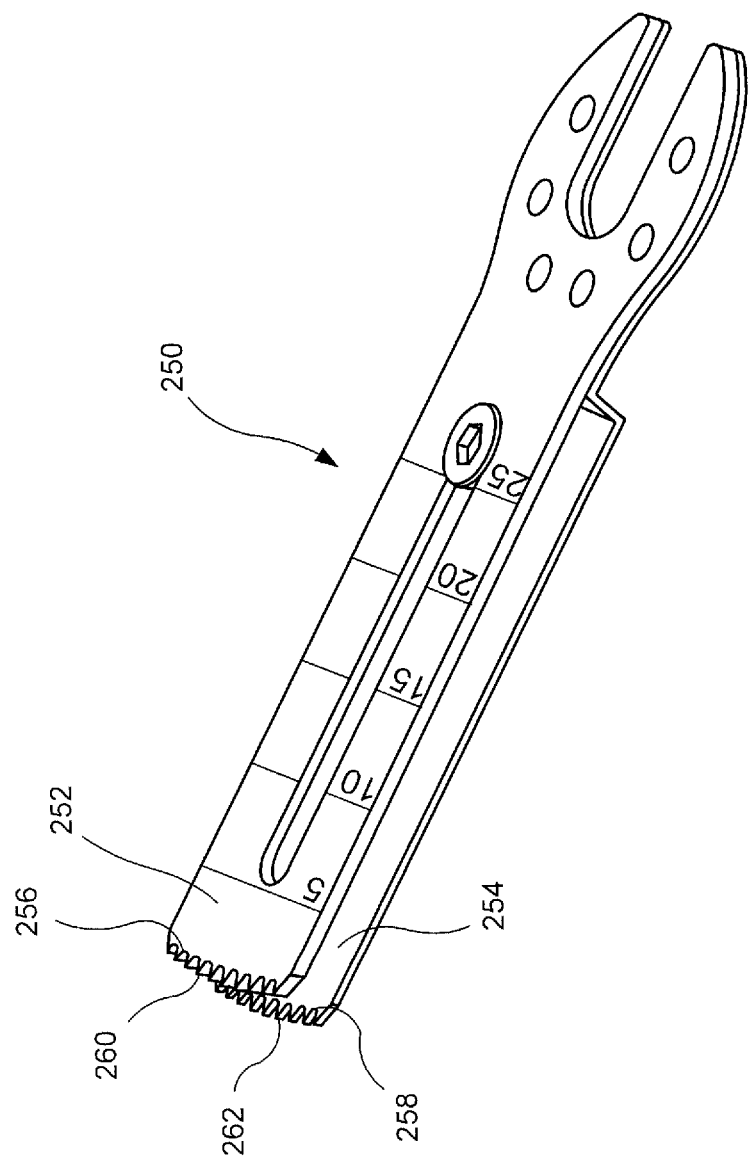
FIG. 16 shows a perspective view of a saw blade according to an exemplary embodiment of the present invention.

An osteotomy system according to a first exemplary embodiment comprises an osteotomy plate 100, as shown in FIGS. 1-8, a drill template 200, as shown in FIG. 11 and a parallel saw 250, as shown in FIG. 16. The system may further comprise a saw guide 222, as shown in FIGS. 13-14 and a guide wire 240, as shown in FIG. 12. The plate 100 may be used to fix portions of a bone (e.g., the ulna) cut using the saw 250 and the drill template 200 and/or the saw guide 222 as a guide. The drill template 200 permits the bone to be pre-drilled, prior to cutting of the bone, with holes corresponding to the locations of openings in the plate 100. The drill template 200 may include markings indicating predefined shortening lengths with holes arranged therein so that, when the template 200 is placed over a target portion of the bone prior to cutting, the holes are aligned with positions which will correspond to the locations of holes in the plate 100 after a portion of the bone has been cut away and during compression of the remaining pieces of bone into contact with one another. That is, the plate 100 includes 2 holes 138 including elongated portions 142 which, when the plate 100 is placed on the bone in a desired orientation, extend substantially parallel to a compression axis (i.e., an axis along which the severed portions of bone will be moved toward one another). Initial bone screws may be inserted through the holes 138 and/or the holes 110 and into the correspondingly pre-drilled holes in the bone to hold the plate 100 on the portions of bone to maintain a desired rotational alignment of the cut portions of bone relative to one another. The initial screw inserted at an end of the elongated portion 142 will then be free to move longitudinally within the elongated portions 142 during compression of the cut bone pieces toward one another to maintain the desired rotational alignment during this compression. The saw 250 includes 2 parallel blades 252, 254 which permit a user to make two simultaneous parallel cuts to remove the desired amount of bone in a single precise action.

As shown in FIG. 1, the plate 100 extends longitudinally from a proximal end 102 to a distal end 104 and includes a first surface 106 which, when in an operative position, faces away from the bone and a second surface 108 which, when in an operative position, faces the bone. The plate 100 includes a plurality of holes including a three-part combination hole 110, a two-part combination hole 138 and a locking hole 148. The plate 100 may include a low profile with tapered and/or rounded proximal and distal ends 102, 104 along with rounded edges to prevent irritation to surrounding tissue. The plate 100 is also pre-bent at an angle of approximately 4° relative to a longitudinal axis thereof to achieve compression at an opposite cortex. The plate 100 may be formed of any biocompatible material including, for example, stainless steel, titanium, etc.

In a preferred embodiment, the plate 100 is symmetrical about an axis of symmetry 150 which extends substantially perpendicularly through a midpoint thereof along a length of the plate 100. Thus, the plate 100 includes a proximal portion 152 proximal of the axis of symmetry 150 that is substantially symmetrical to and/or a mirror image of a distal portion 154 distal of the axis of symmetry 150. It will be understood by those of skill in the art that the symmetrical plate 100 is preferred so that the plate 100 may be positioned along the bone in either orientation. It will also be understood by those of skill in the art that since the plate 100 may be positioned in either orientation along the bone, the terms "proximal" and "distal" as used herein, do not refer to a particular end of the plate 100, but are used to refer to ends which, when in an operative position, are oriented toward the proximal and distal ends of the bone, respectively. In this preferred embodiment, the plate 100 includes two of the three-part holes 110, two of the two-part holes 138 and two of the locking holes 148. In particular, a first three-part hole 110a, a first two-part hole 138a and a first locking hole 148a may be positioned along the proximal portion 152 of the plate 100, while a second three-part hole 110b, a second two-part hole 138b and a second locking hole 148b are positioned in a corresponding symmetrical position along the distal portion 154 of the plate 100. The first and second three-part holes 110a, 110b are, in this embodiment, positioned closest to the axis of symmetry 150 while the locking holes 148a, 148b are furthest from the axis of symmetry 150 and closest to the proximal and distal ends 102, 104, respectively. However, those skilled in the art will understand that different numbers of any of these types of holes may be employed to suit the requirements of a given procedure without deviating from the teachings of the invention.

Figure 5B:
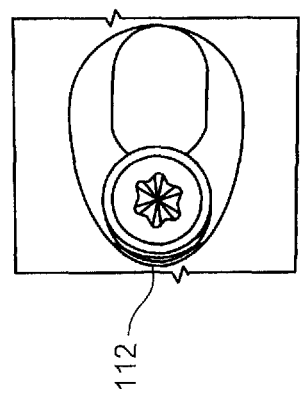
FIG. 5B shows an enlarged cross-sectional view of the three part hole and bone fixation element of FIG. 5A.

As shown in FIGS. 2-4, the three part-hole 110 includes a first portion 112, a second portion 114 and a third portion 116. The first and third portions 112, 116 define opposing longitudinal ends of the three-part hole 110 with the first portion 112 and the third portion 116 connected via the second portion 114. The first portion 112 is defined by a partial circular opening, which tapers radially inward from the first surface 106 toward the second surface 108 in a substantially conical shape. The first portion 112 includes threading 118 along an inner surface 120 thereof and is adapted and configured to receive a first type of bone fixation element 122 (e.g., a locking screw) therethrough along a central axis of the first portion 112, as shown in FIGS. 5A-5B. As would be understood by those skilled in the art, the threading 118 engages a correspondingly threaded head portion 124 of the first bone fixation element 122 as the head portion 124 is rotated therein about the central axis.

Figure 6A:
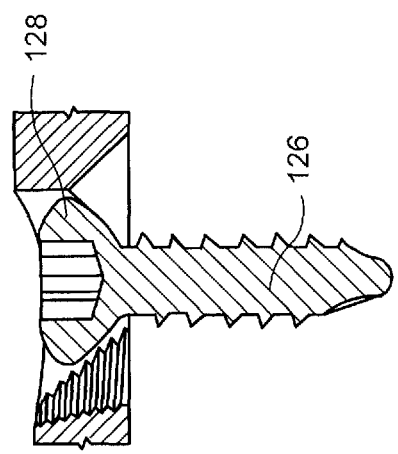
FIG. 6A shows an enlarged top view of the three-part hole of FIG. 2 including a bone fixation element inserted therethrough, in a second configuration.
Figure 6B:
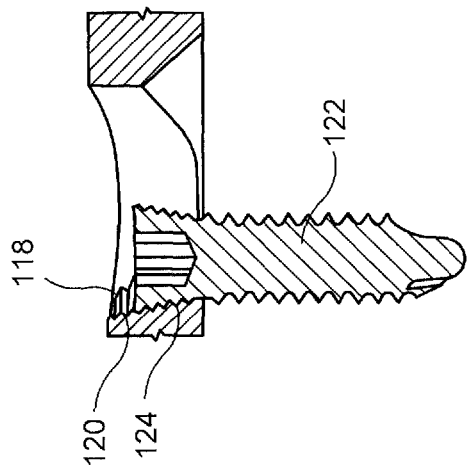
FIG. 6B shows an enlarged cross-sectional view of the three-part hole and bone fixation element of FIG. 6A.

The second portion 114 and the third portion 116 together define a substantially elongated portion of the three-part hole 110 that is adapted and configured to receive a second type of bone fixation element 126 (e.g., a cortex screw) therethrough at any desired angle between 0° and 45° relative to an axis which is substantially perpendicular to a surface of a bone on which the plate 100 is positioned without screw head prominence. The second portion 114 extends between the first portion 112 and the third portion 116, including radially opposed curved walls 130 that taper from the first surface 106 to the second surface 108. The second type of bone fixation element 126 may be inserted into the second portion 114 along the central axis thereof until a correspondingly shaped (e.g., spherical) head portion 128 of the second bone fixation element 126 is seated between the curved walls 130 of the second portion 114, as shown in FIGS. 6A-6B. The curved walls 130 are shaped to receive the head portion 128 and prevent the head portion from extending past the first surface 106. The third portion 116 may overlap with the second portion 114, transitioning smoothly therefrom such that the second type of bone fixation element 126 may be inserted therethrough at an angle up to 45° relative to a central axis thereof. The third portion 116 includes a first inner wall 132 extending into the plate 100 from the first surface 106 to a second inner wall 134 extending from a bone facing end of the first inner wall 132 to the second surface 108. The first inner wall 132 forms a continuous surface with the curved walls 130 of the second portion 114 to accommodate the head portion 128 at a desired angle relative thereto. The second inner wall 134 extends radially outward from the first inner wall 132 to the second surface 108 to accommodate a shaft portion 136 of the second type of bone fixation element 126 at any desired angle up to a maximum angulation. For example, in this embodiment, the second inner wall 134 extends outward from the first inner wall 132 along a longitudinal axis of the plate 100 at an angle of 45°, as shown in FIGS. 7A-7B, permitting the second type of bone fixation element to be inserted therethrough at any angle relative to the surface of the bone between perpendicular and 45°. As will be described in more detail below, when the bone is to be shortened via cuts which are angulated relative to the transverse, it is preferable to make the cuts at an angle no greater than the maximum angulation of the second type of bone fixation element in the third portion 116 of the hole 110. This allows the user to insert the second type of bone fixation element therethrough along an axis perpendicular to the cut in the bone.

The two-part hole 138 includes a first portion 140 and a second portion 142. The first portion 140 in this embodiment is substantially similar to the first portion 112 of the three-part hole 110 and is adapted and configured to receive the first type of bone fixation element 122 along a central axis thereof to engage with the head portion 124 of the bone fixation element 122 via a threading 144 therein. The second portion 142 defines a substantially elongated slot including a curved inner wall 146 that tapers from the first surface 106 toward the second surface 108.

The locking hole 148 includes threading (not shown) along an inner surface thereof for engaging a threaded head portion of a bone fixation element such as a locking screw. The locking holes 148 may be positioned proximate the proximal and distal ends 102, 104 of the plate 100 to anchor the plate 100 to the bone, fixing the plate 100 relative thereto. A first portion of the locking hole 148 extending into the plate 100 from the first surface 106 tapers radially inward toward the second surface 108 to correspond to a shape of the head portion of the locking screw.

It will be understood by those of skill in the art the plate 100 may be manufactured in a variety of lengths including any combination of the holes 110, 138 and 148 described, in a preferably symmetric pattern. For example, a shorter 6-hole plate 100, as shown in FIG. 1, may include two three-part combination holes 110a, 110b, two two-part combination holes 138a, 138b and two locking holes 148a, 148b positioned along a length of the plate 100 in a symmetric pattern. In a longer 8-hole plate 100, as shown in FIG. 8, the plate 100 includes two non-elongated two-part holes 158a, 158b, the non-elongated two-part hole 158a positioned along the proximal portion 152 of the plate 100 while the non-elongated two-part hole 158b is positioned in a corresponding symmetrical position along the distal portion 154. Each of the non-elongated two-part holes 158a, 158b may include a first portion 160 and a second portion 162 that are substantially similar to the two-part hole 138. However, the second portion 162 is non-elongated. Those skilled in the art will understand that, depending on the intended use of a particular plate, the holes need not be distributed symmetrically along a length thereof.

Figure 9:
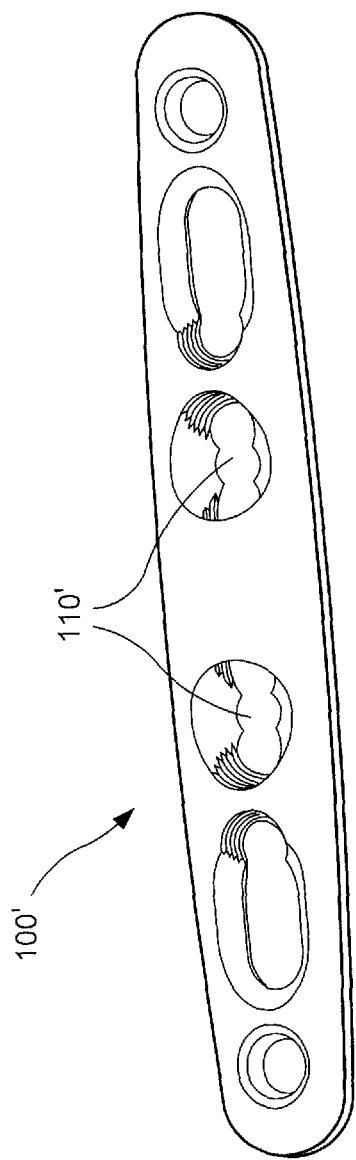
FIG. 9 shows a perspective view of an osteotomy plate according to an alternate embodiment of the present invention.
Figure 10:
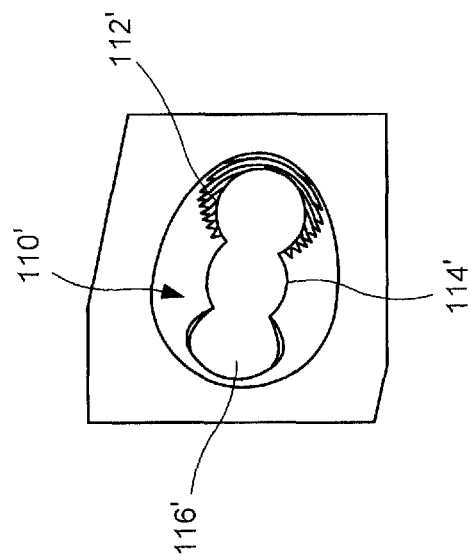
FIG. 10 shows an enlarged perspective view of a three-part hole of the plate of FIG. 9.

According to an alternate embodiment, as shown in FIGS. 9-10, a plate 100' may be substantially similar to the plate 100, including a three-part combination hole 110'. Similarly to the plate 100, the combination hole 110' includes a first portion 112', a second portion 114' and a third portion 116'. However, unlike the hole 110 of the plate 100, the second and third portions 114', 116' are not provided with a smooth transition therebetween. Rather, the second and third portions 114' and 116' are defined by separate distinct rounded openings such that a bone fixation element may only be inserted through one of the second portion 114' and the third portion 116'. Thus, the bone fixation element may be inserted thereinto only along one of a central axis of the second portion 114' at an angle of 0° and a predefined insertion axis of the third portion 116', which is set at an angle (e.g., 45°) relative to a central axis of the three-part hole 110'. The hole 110' does not permit insertion of a bone fixation element therethrough at an angle between the second and third portions 114', 116'.

As shown in FIG. 11, the drill template 200 may extend longitudinally from a proximal end 202 to a distal end 204 and include a first surface 206 which, when in an operative position, faces away from the bone, and a second surface 208 which, when in the operative position, faces the bone. As those skilled in the art will understand, the terms proximal and distal in regard to the drill template 200 correspond only to the orientation of the drill template 200 in its desired orientation in the exemplary procedures. In other procedures the orientation of the components of the drill template may be reversed. The drill template 200 includes a plurality of openings 210 extending through the drill template 200 from the first surface 206 to the second surface 208. The drill template 200 may be manufactured in a variety of predefined shortening lengths (e.g., 2.0, 2.5, 3.0, 4.0 and 5.0 mm) to permit pre-drilling, prior to cutting the bone. Thus, each of the openings 210 is positioned along the drill template 200 at a location corresponding to a position of one of the three-part holes 110 and two-part hole 138. In a preferred embodiment, the drill template 200 includes three openings 210. Two of the openings 210 are positioned toward the distal end 204 of the drill template 200 while one of the openings 210 is positioned toward the proximal end 202—i.e., at a location corresponding to a portion of the bone which will be on the opposite side of the cut from the portion of the bone into which holes will be drilled from the first two openings 210. For example, a first one 210a of the three openings 210 corresponds to a position of the three-part hole 110 along the distal portion 154 of the plate 100 while a second one 210b of the openings 210 corresponds to a position of the two-part hole 138b on the distal portion. A third opening 210c corresponds to a proximal end 146 of the two-part hole 138a extending through the proximal portion 152.

Figure 15:
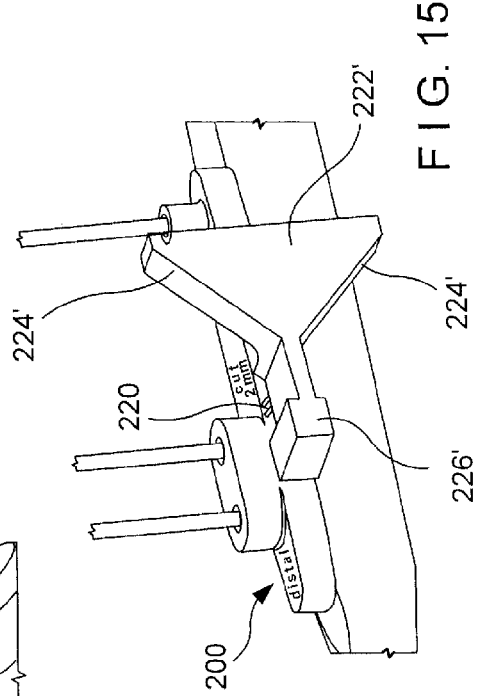
FIG. 15 shows a side view of a saw guide according to an alternate embodiment of the present invention.

The openings 210 are preferably sized and shaped to received a guide wire 240, as shown in FIG. 12, and/or a drill tip therethrough. The drill template 200 further includes protrusions 212 along the first surface 206, which extend from the first surface 206 about each of the openings 210 to permit greater support along a length of the guide wire(s) 240 inserted into the openings 210. The guide wire 240 may include a drill tip 242 at a distal end thereof such that holes may be drilled in the bone via insertion of guide wires 240 through the openings 210. The drill template 200 further comprises an undercut 214 along the second surface 208 which is recessed so that the bone may be fully cut through while the drill template 200 is positioned thereover without having the saw 250 come into contact with the drill template 200. On a lateral side 216 of the undercut 214, the drill template 200 includes markings 218, 220 showing positions at which the bone should be cut. For example, a first marking 218 indicates a substantially transverse cut (e.g., substantially perpendicular to a longitudinal axis of the bone), while a second marking 220 indicates a cut at a desired angle (e.g., 45°) relative to the longitudinal axis of the bone. Thus, the drill template 200 may also provide a guide for the saw 250 such that a separate saw guide may be unnecessary when used to provide a transverse cut of the bone since the blade may be substantially aligned with the markings 218. In cases where it is desirable to use the drill template 200 in combination with a saw guide 222, as further described below, the drill template 200 may include a groove 215 along the first surface 206 to receive a portion of the saw guide 222.

Where the drill template 200 is used to provide an oblique cut via the second markings 220, the system may further comprise the saw guide 222, as shown in FIGS. 13-14, which may be mounted to the drill template 200 to guide the saw 250 along the oblique angle markings. The saw guide 222 may include at least one angled surface 224 which, when the saw guide 222 is mounted to the drill template 200, is aligned with the second markings 220 such that a saw 250 slid along the angled surface will cut the bone at the predefined oblique angle (e.g., 45°). In a preferred embodiment, however, the saw guide 222 may be symmetrical, including two angled surfaces 224 such that the saw guide 222 may be mounted to the drill template 200 to permit the bone to be cut at an oblique angle at indicated markings 220 on both sides of the drill template 200 depending on which side the saw guide 222 is mounted. The saw guide 222 may include an attachment element 228 extending therefrom such that the attachment element 228 may be received within the groove 215 to prevent rotational movement of the saw guide 222 during the cutting. The attachment element 228 may be mounted within the groove 215 of the first surface 206 of the drill template via a screw 226 that is inserted through an opening 230 of the attachment element 228 to be coupled to the first surface 206 of the drill template 200. The saw guide 222 should be attached to the drill template 200 such that the angled surface 224 is aligned with the markings 220 of the drill template 200. In an alternate embodiment, the saw guide 222' may be mounted to the lateral side 216 of the drill template 200 via a pin 226', as shown in FIG. 15, such that an angled surface 224' may be aligned with the second markings 220.

The saw 250, as shown in FIG. 16, comprises a first blade 252 and a second blade 254, each of which is substantially planar and fixed relative to the other such that the first blade 252 and the second blade 254 are substantially parallel to one another. The first and second blades 252, 254 include sharp, bone-cutting distal edges 256, 258, respectively. The sharp distal edges 256, 258, may include teeth 260, 262, respectively, or other features facilitating the cutting of bone as would be understood by those skilled in the art. The saw 250 may be manufactured in any of a variety of sizes for both transverse and oblique cuts in which the first and second blades 252, 254 are separated from one another by a predefined distance corresponding to the predefined shortening lengths of the drill template 200 illustrated via the markings 218, 220. The parallel first and second blades 252, 254 provide a precise parallel cut of the bone in a single cutting action via an oscillating action that drives the saw 250. The saw 250 may be oscillated perpendicular to a longitudinal axis thereof, driving the first and second blades 252, 254 through the bone.

Figure 17:
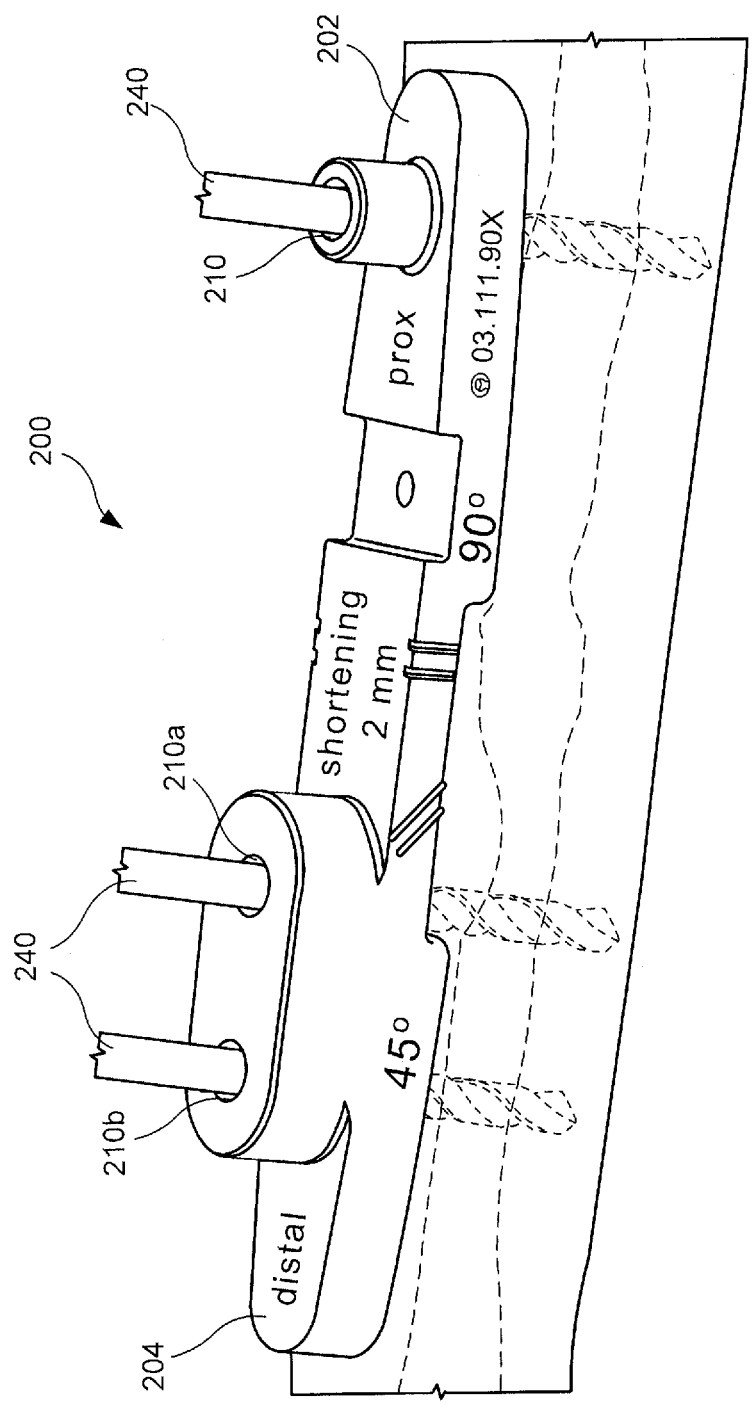
FIG. 17 shows a perspective view of the drill template of FIG. 11 mounted to a bone according to an exemplary embodiment of a surgical technique of the present invention.
Figure 18:
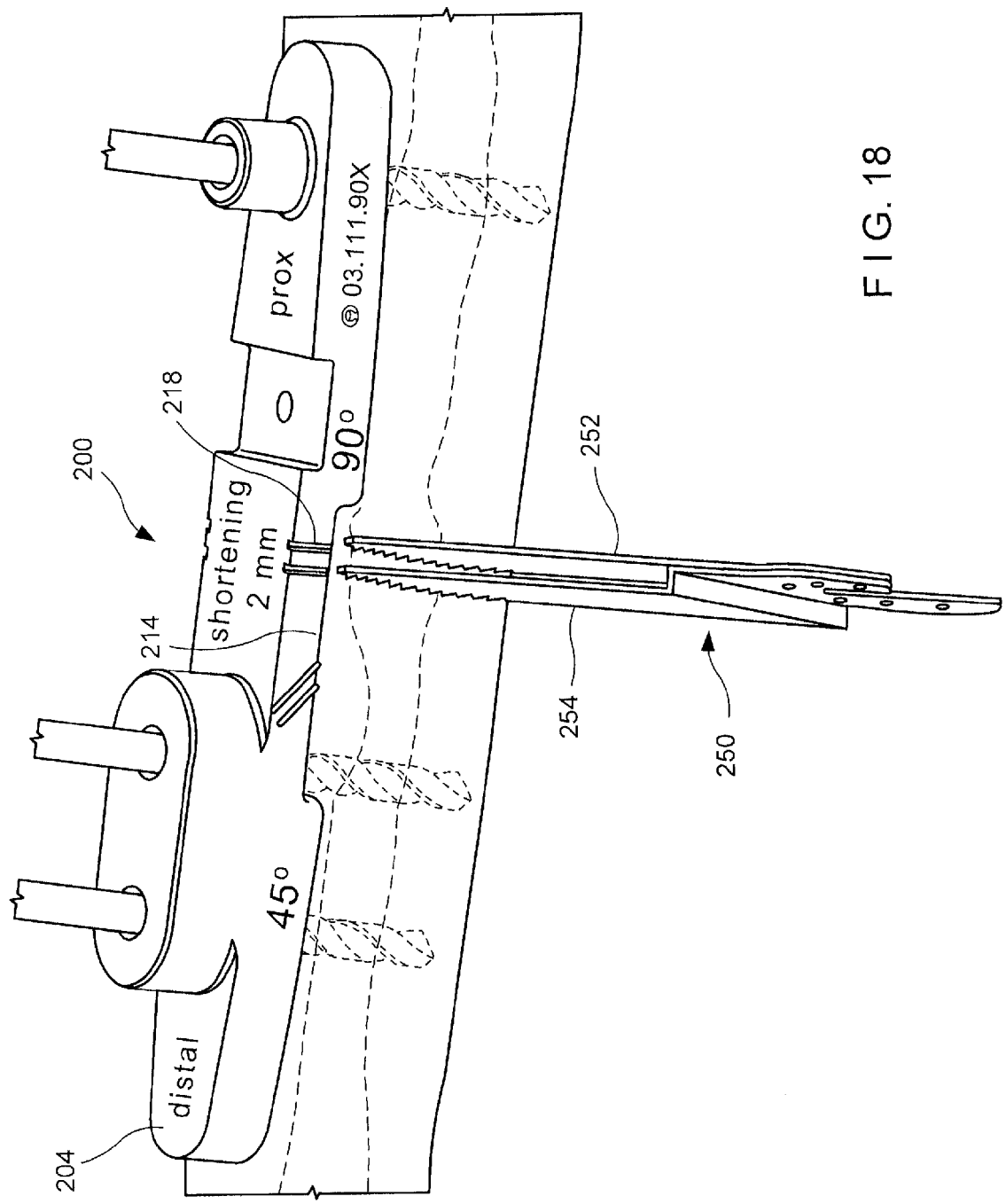
FIG. 18 shows a perspective view of the saw blade of FIG. 16 aligned with transverse markings on the drill template according to the exemplary embodiment of FIG. 17.
Figure 19:
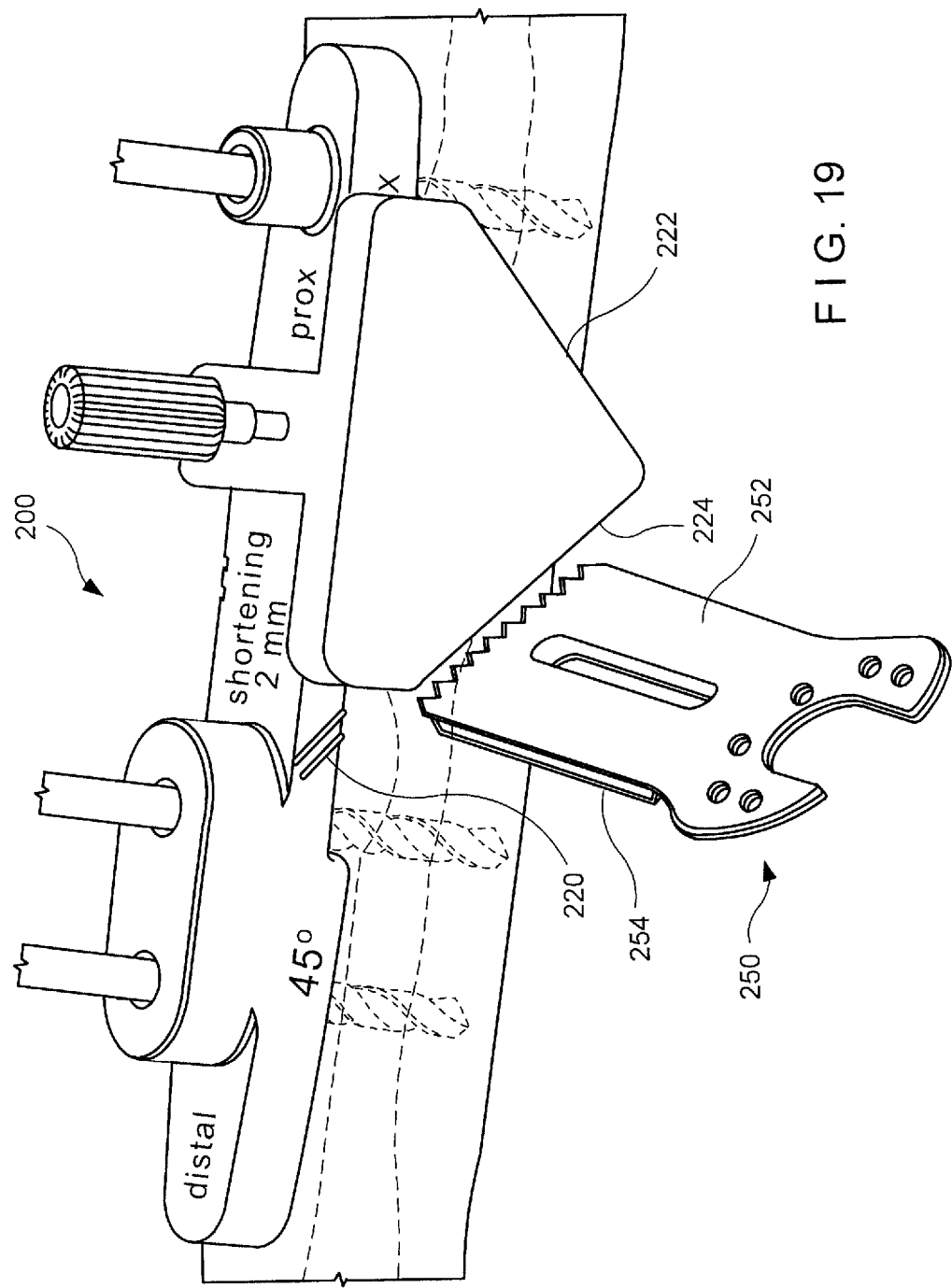
FIG. 19 shows a perspective view of the saw guide of FIG. 14 mounted to the drill template and aligned with oblique markings thereon according to the exemplary embodiment of FIG. 17.

According to an exemplary surgical technique, as shown in FIGS. 17-23, a cut is made in a bone such that the bone may be fixed using the plate 100. As shown in FIG. 17, the drill template 200 is positioned along the bone, preferably along an inner edge of a middle to distal third of the bone (e.g., the ulna) such that the distal end 204 of the drill template 200 faces a distal end of the bone and the proximal end 202 faces a proximal end of the bone. The drill template 200 may be fixed to the bone via guide wires 240 inserted through two or more of the openings 210. The guide wire 240 is inserted in a manner which drills a hole in a corresponding position along the bone via the drill tip 242. It will be understood by those of skill in the art that this pre-drilling facilitates proper alignment of the bone once the bone has been cut. Where a user desires to make a transverse cut through the bone, the first and second blades 252, 254 of the blade 250 are aligned with the first markings 218 indicated on the drill template 200, as shown in FIG. 18. However, where the user desires to the make an oblique cut, the user may attach the saw guide 222 to the drill template 200 and align the angled surface 224 with the second markings 220 such that the saw 250 may be slid therealong, as shown in FIG. 19.

Figure 20:
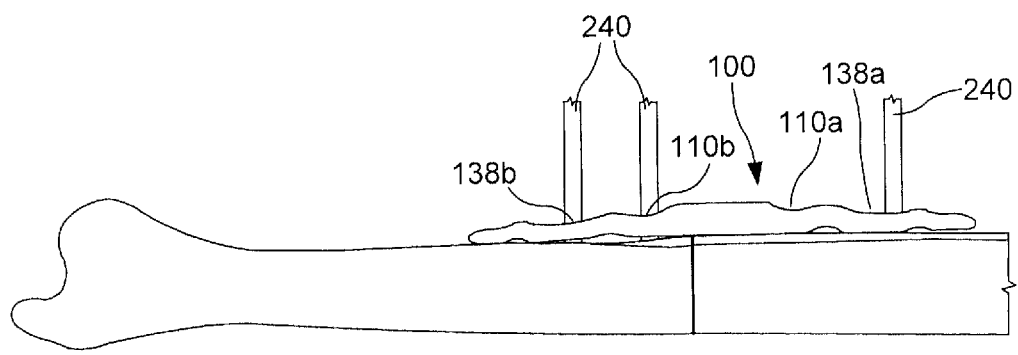
FIG. 20 shows a side view of the plate of FIG. 1 positioned along the bone according to the exemplary embodiment of FIG. 17.
Figure 21:
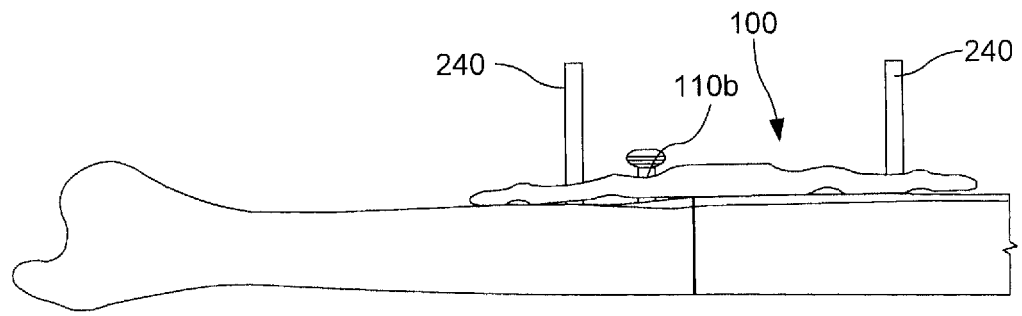
FIG. 21 shows a side view of a first bone fixation element inserted into the plate according to the exemplary embodiment of FIG. 17.
Figure 22:
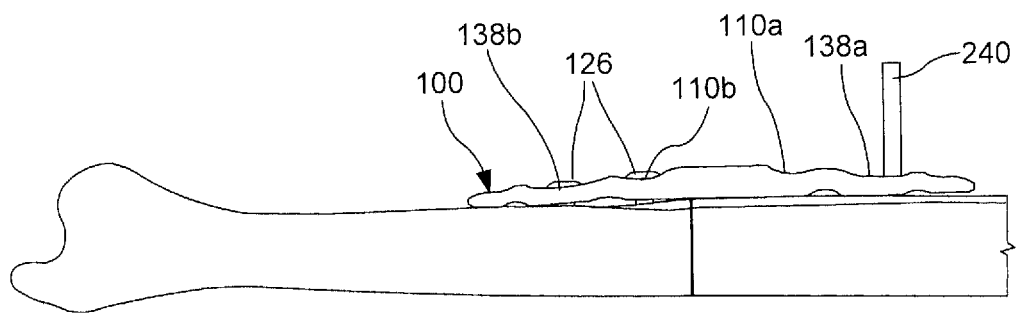
FIG. 22 shows a side view of a second bone fixation element inserted into the plate according to the exemplary embodiment of FIG. 17.

The saw 250 is pressed into the bone to make parallel transverse and/or oblique cuts in the bone. Once the bone has been cut and the cut portion of the bone removed, the drill template 200 is removed, while maintaining insertion of the guide wires 240 in the bone. Upon removal of the drill template 200, the plate 100 is slid over the guide wires 240 onto the bone such that each of the guide wires 240 is received in a corresponding one of the holes 110 and 138 of the plate, as shown in FIG. 20. As shown in FIG. 21, the guide wire 240 initially inserted into the opening 210a which corresponds to the three-part hole 110b of the plate 100, is then removed so that a first one of the second type of bone fixation elements 126 may be inserted therethrough. The guide wire 240 initially inserted into the opening 210b is then removed, as shown in FIG. 22 so that a second one of the second type of bone fixation elements 126 may be inserted into the corresponding two-part hole 138b along the distal portion 154 of the plate 100.

Figure 23:
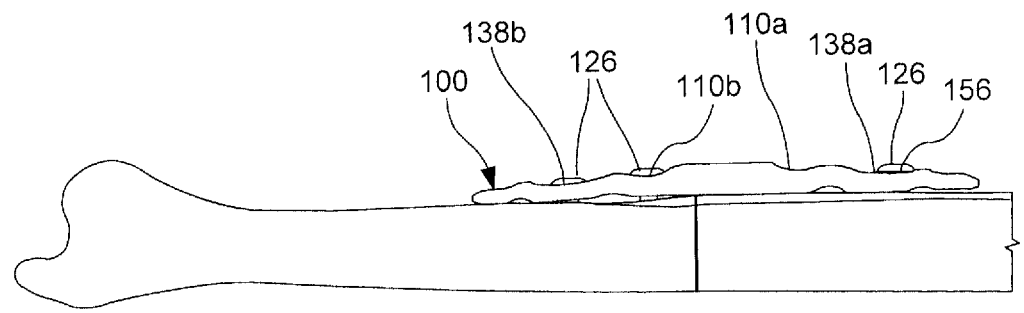
FIG. 23 shows a side view of third bone fixation element inserted into the plate according to the exemplary embodiment of FIG. 17.
Figure 24:
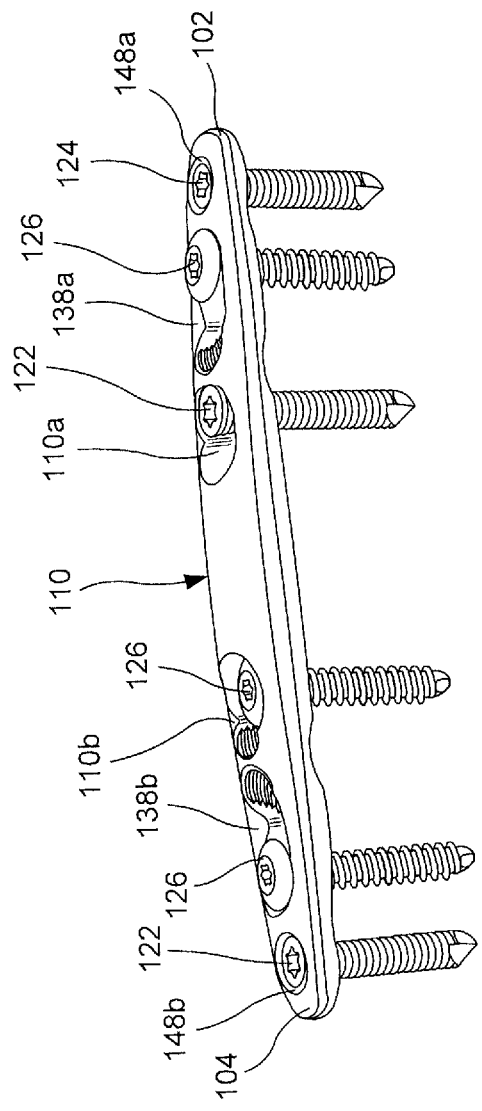
FIG. 24 shows a perspective view of the plate of FIG. 1, as used to fix a transverse cut of the bone according to the exemplary embodiment of FIG. 17.
Figure 25:
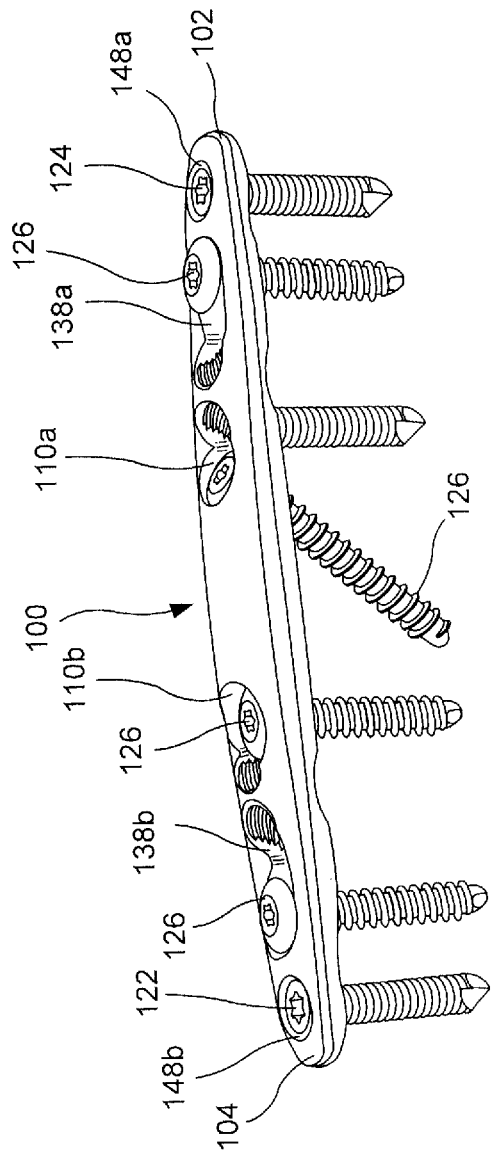
FIG. 25 shows a perspective view of the plate of FIG. 1 as used to fix an oblique cut of the bone according to the exemplary embodiment of FIG. 17.

Finally, the last guide wire 240 is removed, as shown in FIG. 23, and a third one of the second type of bone fixation elements 126 is inserted into the proximal end 156 of the two-part hole 138a on the proximal portion 152 of the plate 100 and through the pre-drilled hole in the bone. Compression is applied to the bone such that a proximal portion of the bone is moved toward a distal portion of the cut bone until the two portions of bone are in a desired spatial relation to one another (e.g., contacting one another at a desired rotational alignment). The proximal portion of the bone may be moved relative to the plate 100 via sliding of the bone fixation element from the proximal end 156 through the elongated second portion 142 of the two-part hole 138a in the proximal portion 152 of the plate 100. Fixation of the bone is then completed by inserting bone screws into the bone through remaining holes of the plate 100. For example, the first type of bone fixation element 122 (e.g., locking screws) may be inserted into the locking holes 148a, 148b and one of the first and the second types of bone fixation elements 122, 126 (e.g., locking screw, cortex screw) may be inserted into the three-part hole 110a, as shown in FIG. 24. Where an oblique cut was made in the bone, the second type of bone fixation element 126 may be inserted through the three-part hole 110a, at an angle relative to the central axis thereof, such that the shaft portion 136 extends through obliquely cut surfaces of the bone, as shown in FIG. 25.

According to a second exemplary embodiment of the present invention, as shown in FIGS. 26-32, a plate 300, as shown in FIG. 26 may be used to fix portions of a bone that have been cut using a drill guide 400 and a saw blade 450. The plate 300, as shown in FIG. 26, is substantially similar to the plate 100, as described above, extending longitudinally from a proximal end 302 to a distal end 304. Similarly to the plate 100, in a preferred embodiment, the plate 300 includes a proximal portion 352 and a distal portion 354 which may be substantially symmetrically shaped relative to one another about an axis of symmetry 350. The plate 300, however, does not include three and two-part combination holes. Rather, the plate 300 includes a plurality of locking holes 310 extending therethrough from a first surface 306 to a second surface 308 along both the proximal and distal portions 352, 354. For example, the proximal portion 352 may include a plurality of locking holes 310a and the distal portion 354 may also include a plurality of locking holes 310b. As shown in FIG. 26, however, the plurality of locking holes 310a, 310b are not required to mirror one another along the proximal and distal portions 352, 354. Additionally, the proximal portion 352 and the distal portion 354 may each include an elongated hole 338a, 338b, respectively.

The locking holes 310 may be substantially similar to the locking holes 148, including threading 318 extending about an inner surface thereof for engaging a threaded head portion of a bone fixation element. The elongated hole 338 may be elongated in a longitudinal direction, including an inner surface 346 that tapers from the first surface 306 toward the second surface 308. The inner surface 346 may be substantially spherically shaped to receive a correspondingly shaped head portion of a bone fixation element such as, for example, a cortex screw.

As shown in FIG. 27, the drill template 400 may be substantially similar to the drill template 200, as described above, extending from a proximal end 402 to a distal end 404 and including openings 410 corresponding to the positions of the locking holes 310b in the distal portion 354 and the elongated hole 338a in the proximal portion 352. Similarly to the drill template 200, the drill template 400 may be positioned along the bone to pre-drill holes in the bone using a guide wire or a drill tip 440 inserted through the openings 410 at positions corresponding to the positions at which the holes 310b, 338a extending through the plate 300 will be located when the plate 300 is in a desired position over the severed portions of the bone after it has been cut. The saw 450, which is substantially similar to the saw 250, may be subsequently used to make a parallel transverse and/or oblique cut in the bone using a saw guide 422 which may be positioned against the bone in the same manner described above. As shown in FIG. 28, the saw guide 422 may be positioned against the bone to make a substantially transverse cut therethrough. Alternatively, the saw guide 422 includes angled surfaces 424 such that the saw 450 may be moved against the angled surface to cut the bone along a predefined oblique angle relative to the axis of the bone.

Figure 30:
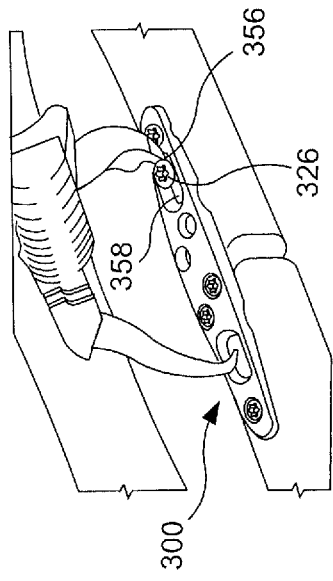
FIG. 30 shows a perspective view of a compression of the bone according to the exemplary embodiment of FIG. 26.
Figure 32:
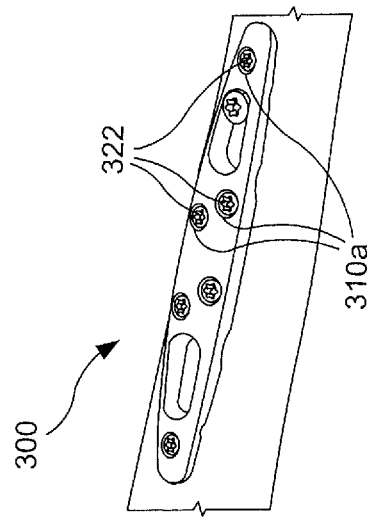
FIG. 32 shows a perspective view of additional bone fixation elements inserted into the bone plate of FIG. 26.
Figure 29:
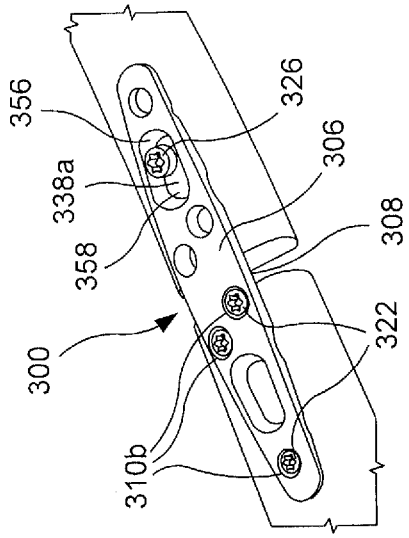
FIG. 29 shows a perspective view of the bone plate positioned along the bone according to the exemplary embodiment of FIG. 26.
Figure 31:
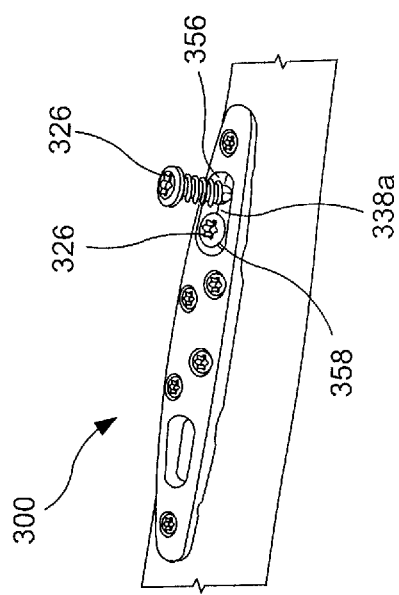
FIG. 31 shows a perspective view of a bone fixation element inserted into the bone plate of FIG. 26.

A surgical technique according to the system of the second exemplary embodiment is substantially similar to the technique described above. Subsequent to cutting the bone, the drill template 400 is removed and the plate 300 is slid over the guide wires 440 and positioned along the bone. Alternatively, the guide wires and/or drill tip 440 may be removed after the holes have been pre-drilled in the bone. Upon removal of the guide wires 440, bone fixation elements 322 of the first type (e.g., locking head screws) are inserted into the locking holes 310b along the distal portion 354, as shown in FIG. 29 and a bone fixation element 326 of the second type (e.g., a cortex screw) may be inserted into a proximal end 356 of the elongated hole 338a in the proximal portion 352. Compression is then applied to the bone to move a proximal portion of the bone toward a distal portion thereof until the proximal and distal portions of the severed bone are in a desired spatial relation to one another, as shown in FIG. 30. During this movement, the bone fixation element 326, which was inserted through the proximal end 356 of the elongated hole 338a, slides distally within the elongated hole 338a toward a distal end 358 thereof. For additional compression, a second bone fixation element 326 may be inserted into the proximal end 356 of the elongated hole 338a, as shown in FIG. 31. To provide further fixation, additional bone fixation elements 322 may be inserted into the remaining locking holes 310a, as shown in FIG. 32.

It will be apparent to those skilled in the art that various modifications and variations can be made in the structure and the methodology of the present invention, without departing from the sprit or the scope of the invention. Thus, it is intended that the present invention cover the modifications and variations of this invention provided that they come within the scope of the appended claims and their equivalents.

What is claimed is:

1. A bone plate, comprising:
   an elongated body extending from a proximal end to a distal end and including a first surface which, when in an operative position, faces away from a bone on which the plate is to be mounted and a second surface which, when in the operative position, faces the bone, the elongated body including a proximal portion and a distal portion symmetrical about an axis perpendicular to a longitudinal axis of the bone plate to the proximal portion;
   a first three-part combination hole extending through the proximal portion of the plate and a second three-part combination hole extending through the distal portion of the plate, a first portion thereof being threaded and configured to engage a threaded head portion of a bone fixation element, a second portion thereof configured to receive a bone fixation element along an axis perpendicular to a longitudinal axis of the bone when the plate is mounted thereon in a desired orientation and a third portion defining a screw axis extending from the second surface toward the distal end of the elongated body at a non-perpendicular angle relative to the longitudinal axis of the bone when the plate is mounted thereon in a desired orientation, wherein the first and second three-part combination holes are equidistant from the axis of symmetry; and
   a first two-part combination hole extending through the proximal portion of the plate and a second two-part combination hole extending through the distal portion of the plate, a first threaded portion thereof being configured to receive and engage a threaded head portion of a bone fixation element and a second portion thereof defining an elongated slot extending along a longitudinal axis of the plate for receiving a bone fixation element therethrough so that when the first and second two-part combination holes and the first three-part combination hole engage respective bone fixation elements, the plate configured to slide along its longitudinal axis relative to the bone fixation element received through the second two-part combination hole, wherein the first and second two-part combination holes are equidistant from the axis of symmetry.

2. The plate of claim 1, further comprising a first threaded locking hole extending through a distal portion of the elongated body, the first locking hole including a threading along an inner surface thereof for threadedly engaging a threaded head of a bone fixation element.

3. The plate of claim 1, wherein the third portion of the first three-part hole includes a first wall extending from the first surface toward the second surface and a second wall extending outward along the longitudinal axis of the bone plate from an end of the first wall to the second surface.

4. The plate of claim 1, wherein the second and third portions of the first three-part hole overlap such that a bone fixation element is receivable therebetween at any user-selected angle relative to the longitudinal axis of the bone between 90 degrees and the non-perpendicular angle.

5. The plate of claim 4, wherein the non-perpendicular angle is 45°.

6. The plate of claim 1, further comprising:
a non-elongated two-part combination hole extending through at least one of the proximal portion and the distal portion of the plate, a first threaded portion thereof being configured to receive and engage a threaded head portion of a bone fixation element and a second portion thereof defining a non-elongated slot for receiving a bone fixation element therethrough.

7. An osteotomy system, comprising:
a bone plate, including:
an elongated body extending from a proximal end to a distal end and including a first surface which, when in an operative position, faces away from a bone on which the plate is to be mounted and a second surface which, when in the operative position, faces the bone, the elongated body including a proximal portion and a distal portion symmetrical about an axis perpendicular to a longitudinal axis of the bone plate to the proximal portion;
a first three-part combination hole extending through the proximal portion of the plate and a second three-part combination hole extending through the distal portion of the plate, a first portion thereof being threaded and configured to engage a threaded head portion of a bone fixation element, a second portion thereof configured to receive a bone fixation element along an axis perpendicular to a longitudinal axis of the bone when the plate is mounted thereon in a desired orientation and a third portion defining a screw axis extending from the second surface toward the distal end of the elongated body at a non-perpendicular angle relative to the longitudinal axis of the bone when the plate is mounted thereon in a desired orientation, wherein the first and second three-part combination holes are equidistant from the axis of symmetry; and
a first two-part combination hole extending through the proximal portion of the plate and a second two-part combination hole extending through the distal portion of the plate, a first threaded portion thereof being configured to receive and engage a threaded head portion of a bone fixation element and a second portion thereof defining an elongated slot extending along a longitudinal axis of the plate for receiving a bone fixation element therethrough so that the plate configured to slide along its longitudinal axis relative to the bone fixation element received therethrough, wherein the first and second two-part combination holes are equidistant from the axis of symmetry; and
a drill template, including:
a longitudinal member extending from a proximal end to a distal end and including a first surface which, when in an operative, position faces away from a bone on which the plate is to be mounted and a second surface which, when in an operative position, faces a bone on which the plate is to be mounted, a length of the longitudinal member including markings indicating a predefined shortening length of the bone; and
a plurality of openings extending therethrough at locations corresponding to locations at which one of the first and second three-part holes and both the first and second two-part holes of the bone plate will be located after a predetermined portion of the bone has been removed.

8. The osteotomy system of claim 7, further comprising a locking hole extending through the elongated body from the first surface to the second surface, the locking hole including threading along an inner surface thereof for engaging a corresponding threading on a head of a bone screw to be inserted therethrough.

9. The osteotomy system of claim 7, wherein the second and third portions of the first three-part hole overlap such that a bone fixation element is receivable therein at any user-selected angle between 90 degrees and the non-perpendicular angle.

10. The osteotomy system of claim 7, further comprising a saw including first and second blades substantially parallel to one another and separated by a distance corresponding to a predefined length by which a bone is to be shortened.

11. The osteotomy system of claim 10, further comprising a saw guide attachable to the drill template, the saw guide including an angled surface to guide the saw blade, when the drill template is in the operative position, along a desired oblique angle relative to a longitudinal axis of a bone on which the plate is to be mounted.

12. The osteotomy system of claim 11, wherein the saw guide is attachable to the first surface of the drill template via a fixation screw.

13. The osteotomy system of claim 11, wherein the drill template includes a notch in a first surface thereof sized to non-rotatably receive the saw guide.

14. The osteotomy system of claim 11, wherein the saw guide includes an attachment element extending therefrom for attachment to the first surface of the drill template.

15. The osteotomy system of claim 7, wherein the longitudinal member of the drill template includes an undercut along the second surface thereof at a location which, when the drill template is in the operative position, overlies a portion of bone to be removed.

16. The osteotomy system of claim 7, wherein the longitudinal member of the drill template includes a marking on a lateral surface thereof showing locations at which a bone is to be cut to obtain a desired shortening thereof.

17. The osteotomy system of claim 16, wherein the markings indicate one of a transverse cut and an oblique cut.

18. The osteotomy system of claim 7, further comprising a guide wire including a drill tip for inserting through the plurality of openings of the drill template to pre-drill the bone at locations and along axes determined by the openings in the drill template.

* * * * *